(12) United States Patent
Tucker et al.

(10) Patent No.: US 6,330,470 B1
(45) Date of Patent: Dec. 11, 2001

(54) METHOD FOR LOCALIZING ELECTRICAL ACTIVITY IN THE BODY

(75) Inventors: Don M. Tucker; Thomas C. Ferree, both of Eugene; K. Jeffrey Ericksen, Portland, all of OR (US)

(73) Assignee: Electrical Geodesics, Inc., Eugene, OR (US)

( * ) Notice: Subject to any disclaimer, the term of this patent is extended or adjusted under 35 U.S.C. 154(b) by 0 days.

(21) Appl. No.: 09/466,583

(22) Filed: Dec. 17, 1999

(51) Int. Cl.[7] ........................................................ A61B 5/04
(52) U.S. Cl. ............................ 600/544; 600/546; 600/547
(58) Field of Search .................................. 600/544, 545, 600/546, 547

(56) References Cited

U.S. PATENT DOCUMENTS

| | | |
|---|---|---|
| 4,202,354 | 5/1980 | Smith et al. . |
| 4,204,546 | 5/1980 | Smith et al. . |
| 4,236,511 | 12/1980 | Loeb . |
| 4,409,987 | 10/1983 | McIntyre . |
| 4,411,273 | 10/1983 | John . |
| 4,417,590 | 11/1983 | Smith et al. . |
| 4,424,816 | 1/1984 | Callahan et al. . |
| 4,690,149 | 9/1987 | Ko . |
| 4,736,751 | 4/1988 | Gevins et al. . |
| 4,819,648 | 4/1989 | Ko . |
| 5,263,488 | * 11/1993 | Van Veen et al. ................. 128/731 |
| 5,291,888 | * 3/1994 | Tucker ................................ 128/644 |
| 5,458,117 | 10/1995 | Chamoun et al. . |
| 5,501,230 | 3/1996 | Laribiere . |
| 5,611,350 | * 3/1997 | John ................................... 128/731 |
| 5,807,270 | 9/1998 | Williams . |
| 5,816,247 | 10/1998 | Maynard . |

* cited by examiner

Primary Examiner—Eric F. Winakur
Assistant Examiner—Patricia Mallari
(74) Attorney, Agent, or Firm—Birdwell, Janke & Durando, PLC

(57) ABSTRACT

A method for localizing electrical activity in the body. A plurality of electrical devices apply a predetermined current (or voltage) to the surface of the body, and sense voltage (or current). The same electrical devices employed to sense voltage (or current) from sources of electrical activity within the body are also employed to sense voltage (or current) that results from the application of current (or voltage) by the other electrical devices. The voltages (or currents) sensed are used to characterize impedance within the body as well as to localize sources of the electrical activity.

8 Claims, 1 Drawing Sheet

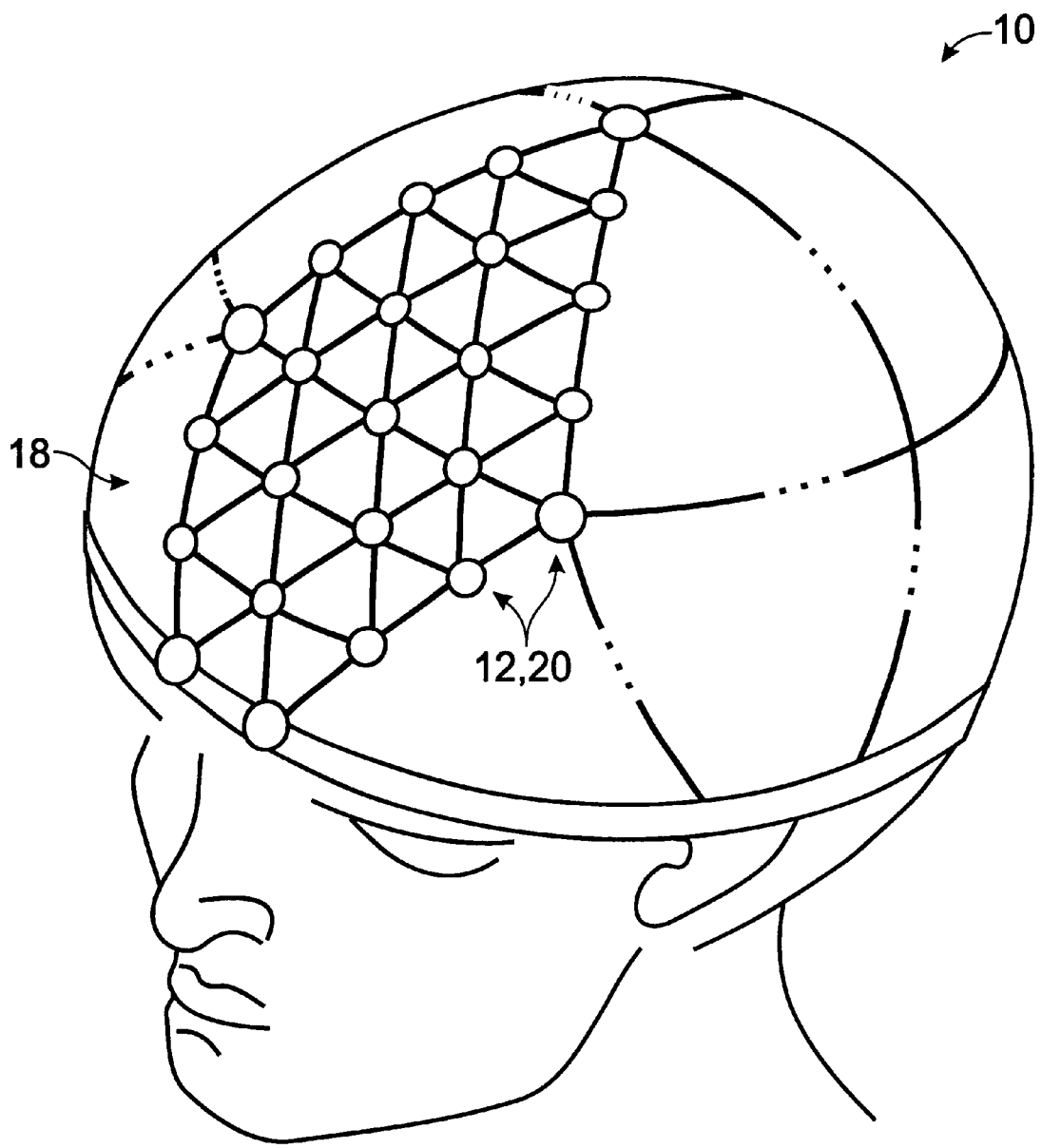

METHOD FOR LOCALIZING ELECTRICAL ACTIVITY IN THE BODY

BACKGROUND OF THE INVENTION

The present invention relates to bioelectrical measurement, particularly to a method for localizing electrical activity in the body, such as in the brain or heart.

As is well known, the body produces electrical fields and waves, and these provide important information regarding body function. To acquire this information, it is often necessary and usually desirable to determine the sources of electrical energy inside the body whose electrical effects are measured at the body surface. Conventional source analysis begins by measuring the electrical potential at the surface of the body proximate an underlying organ of interest. For analyzing sources in the heart, an electrocardiograph ("ECG") measures the electrical potential on the torso, while for analyzing sources in the brain, an electroencephalograph ("EEG") measures the electrical potential on the head.

To localize the sources in the organ or tissue that are responsible for given measured surface potentials, a computer-based model is made of the organ or tissue in terms of the conductive paths leading therefrom to the body surface. Ideal sources, such as single or multiple dipoles or extended dipolar sheets, are modeled in the computer and manipulated within a model of the organ or tissue while surface potentials are calculated until satisfactory agreement is reached between the calculated values of potential and those actually measured on the body. Such models require specification of both the body geometry and the body impedance or conductivity as a function of position within the body.

In conventional EEG models, the head is represented by a small number of spherically concentric tissue layers or regions, typically divided as brain, cerebrospinal fluid, skull and scalp, simplifying the model so as to require only four impedance values, one value for each region. In conventional ECG models, the torso is similarly considered to consist of the heart, lung, body cavity and skeletal muscle. Such models make use of impedance values that have been estimated by measuring laboratory subjects.

The advent of magnetic resonance imaging techniques now provides for more geometrically detailed head and torso models, and consequently more precise source localization should be possible. Accordingly, the art has begun to focus on obtaining more precise measurements of impedance of bodily tissue for use in the published tables. However, the increased precision has not translated to the expected degree of increased accuracy. The reason for this has not heretofore been understood.

Accordingly, there is a need for a method for localizing electrical activity in the body that provides for further reducing source localization errors.

SUMMARY OF THE INVENTION

The method for localizing electrical activity in the body of the present invention solves the aforementioned problems and meets the aforementioned needs by providing a plurality of electrical devices on a carrier which distributes the devices over and applies the devices to a selected portion of the surface of the body. The carrier is preferably the geodesic net described in the inventor's U.S. Pat. No. 5,291,888. Each of the devices is adapted to sense voltage (or current), and to apply current (or voltage) at substantially the same location on the body. One of the devices forms a first port with a reference device for applying an input current (or voltage) to the body. Another of the devices forms a second port with the reference device for sensing the resulting voltage (or current).

With a number of current (or voltage) inputs and voltage (or current) outputs distributed over the surface of the body, a best-fit computer model is employed to estimate the conductivity of the underlying tissue as a function of position. Measured potentials of the electrical activity within the body, i.e., without applying current (or voltage) by the devices, are employed to localize the sources of that activity within the body in a standard manner, using the aforedescribed estimates of body conductivity.

Measured potentials for source localization are taken at substantially the same locations as measured potentials for impedance characterization. In some applications, the potentials for both purposes are also taken at substantially the same time.

Therefore, it is a principal object of the present invention to provide a novel and improved method for localizing electrical activity in the body.

It is another object of the present invention to provide such a method that further reduces source localization errors.

The foregoing and other objects, features and advantages of the present invention will be more readily understood upon consideration of the following detailed description of the invention, taken in conjunction with the following drawings.

BRIEF DESCRIPTION OF THE DRAWING

The FIGURE is a schematic of an apparatus for carrying out a method for localizing electrical activity in the body according to the present invention.

DETAILED DESCRIPTION OF A PREFERRED EMBODIMENT

A preferred method for localizing electrical activity in the body according to the present invention is described below. Typically, such methods will be employed to localize sources of electrical activity in the brain or in the heart of human beings. However, the method applies equally well to localizing sources of electrical activity in other organs or body tissue, in humans, other animals or even plants, and will undoubtedly have applicability to localizing electromagnetic activity in inanimate objects as well. The methods of the present invention are, therefore, not limited to application.

Referring to the FIGURE, both in the prior art and according to the present invention, sensors 12 are distributed over a selected portion of the surface of the body 10 of an individual. The sensors 12 are assembled in a carrier 18 which spaces the sensors apart from one another in a predetermined manner. A preferred carrier is that described in Tucker, U.S. Pat. No. 5,291,888 (hereinafter the "geodesic sensor net"), the entirety of which is incorporated herein by reference. The geodesic sensor net places a sensor at the vertices of geodesic triangles by elastic lines connecting the sensors in a mutually-balanced tension network. Preferably, the array includes 128 or 256 sensors with approximately equal spacing between adjacent pairs. A greater number of sensors provides for a greater spatial resolution.

The sensors are typically adapted to sense voltage, but they could be adapted to sense current as well. To simplify discussion, the sensors will be described herein as being adapted to sense voltage, the complementarity of voltage and current being understood.

The sensors functioning together to sense their respective voltages provide a map of potential as a function of location on the body surface. This potential function may be determined for an instant or as a function of time.

To localize the sources inside the body that are responsible for the measured potential function, a computer "body model" is made of the interior of the body. In the body model, the body is partitioned into a number of homogeneous tissue volumes of differing tissue types. The body model may be relatively simple, assuming for example a small number of concentric spherical shells of the differing tissue types, or the body model may be more complex, such as a finite-element model. Voltage sources, the number and strengths of which must be selected by trial and error, are also modeled, typically as single or multiple dipoles, or extended dipolar sheets, and mathematically placed within the body model.

The computer then calculates the potential that would result at the surface of the body model with the given sources and this result is compared to the actual, measured potential function on the body 10. Where there is disagreement, the sources are iteratively moved and/or their characteristics are adjusted to reduce the error to an acceptable level. This modeling process is well known in the art and further details are omitted as not being necessary for understanding.

To calculate the potential that would result at the surface of the body model from the modeled sources requires specification of the conductivity or, more generally, the impedance, of the modeled tissue. Where the model is a simple model, a small number of different impedance values is required. Where the model attempts greater resolution, a larger number of impedance values is required, each being characteristic of a particular volume of the body model.

In the prior art, these impedance values are typically measured by researchers and published as data for inclusion in the computer body model. As published values obtained from measurements on a small number of individuals, the impedance values are not generally correct for the particular body 10.

According to the present invention, the sensors 12 are replaced with electrical devices 20 adapted both for measuring voltage (or current) and applying current (or voltage). The devices 20 are typically adapted to sense voltage, typically in the microvolt range, and apply current, typically in the microamp range. However, the devices may be adapted to sense current and apply voltage as well. To simplify discussion, the devices will be described as sensing voltage and applying current, the complementarity of voltage and current being understood.

The electrical devices 20 may be simple metal electrodes suitably coupled to a suitable volt-meter and current source. The electrical devices 20 are employed in a measurement mode just as the prior art sensors 12. However, in an injection mode, the electrical devices apply a current to the surface of the body.

More particularly, each electrical device forms a port with a selected reference device. According to the invention, some of the ports are employed for sensing the potential on the surface of the body resulting from electrical activity within the body, as in the prior art. These same ports are also employed for sensing the potential on the surface of the body resulting from injecting current into the remaining ports. This latter step provides data for characterizing the impedance of the body volume in an analogous manner to that aforedescribed for characterizing the locality of sources.

That is, a computer "body model" is made of the interior of the body. In the body model, the body is partitioned into a number of homogeneous tissue volumes of differing tissue types. The body model may be relatively simple, assuming for example a small number of concentric spherical shells of the differing tissue types, or the body model may be more complex, such as a finite-element model. Characteristic impedance values, which must be selected by trial and error, are used to characterize the tissue volumes.

The computer then calculates the potential that would result at the surface of the body model with the given distribution of current injection and this result is compared to the actual, measured potential function on the body 10. Where there is disagreement, the modeled impedance values are iteratively adjusted to reduce the error to an acceptable level. This general modeling process is well known in the art and further details are omitted as not being necessary for understanding.

The aforementioned current injection is preferably performed at a frequency or frequencies selected to be distinct from the frequency or frequencies of known body sources, so that the corresponding voltages sensed can be identified as resulting from the injected current. Once impedance values for the body 10 are obtained for use in the body model, the aforementioned prior art localization method may be employed.

According to the present invention, if both the impedance characterization method and the localization method described above are carried out with the same apparatus, i.e., the same carrier 18 and electrical devices 20, significant and unexpected improvements in localization accuracy are obtained. The insight for this recognition stems from the reciprocity theorem. That theorem basically says, for a passive network, that if injecting a current into (or applying a voltage across) a first port produces a voltage (or current) at a second port in response, the same voltage (or current) would be produced at the first port if the same current was injected into (or the same voltage was applied across) the second port. An application of the reciprocity theorem would be that, in the aforedescribed method for characterizing impedance, current injection will only need to occur in half of the electrical devices 20, the other half sensing the resulting voltage, because the two halves form reciprocal pairs.

On the other hand, for a mass of body tissue with an electrical source buried inside, and therefore inaccessible to either sensing voltage or injecting current, the theorem is not rigorously applicable. Nonetheless, it has provided the inventors an important insight. That is, the same conductive paths inside the mass of body tissue are used for conducting current from a source of electrical activity thereinside to the surface, as are used in conducting current injected at the surface to the electrical source. But, injecting current at the body surface is just the aforedescribed method of impedance characterization. Accordingly, so long as the same electrical devices are used in potential measurement for impedance characterization as in potential measurement for source localization, the impedance characterization is automatically tailored to account for the precise electrical pathways inside the body mass, from the electrical sources there, to the surface of the body mass where a potential measurement is made for purposes of source localization. Where the method is carried out in this way, one does not need to know about the details of the body mass to localize sources therein to an accuracy which is limited only by the resolution provided by the number of electrical devices employed.

In fact, some variation between the points of potential measurement for purposes of impedance characterization and the corresponding points of potential measurement for source localization is acceptable; however, the errors have been found to increase non-linearly with separation. Accordingly, it is considered preferable to maintain these points within about one millimeter, though greater variations and therefore greater errors may be accepted without departing from the principles of the invention. In that regard, it should be noted that the error due to variation between the points for impedance characterization and the corresponding points for source localization is greater where there are a greater number of the electrical devices 20 at which measurements are being made.

Alignment of the sensors is provided automatically by electrical devices 20 that are adapted for both measurement and application in conjunction with a carrier 18 that substantially fixes the locations of the electrical devices on the body for at least the period of time during which both sets of measurements are being made.

The most direct application of methods according to the present invention is to determine regional tissue impedance within the methods otherwise described in Eyuboglu, Pilkington and Wolf, "Estimation of Tissue Resistivities From Multiple-Electrode Impedance Measurements", *Phys. Med. Biol.* 39: 1–17 (1994); Eriksen, "In Vivo Head Regional Conductivity Estimation Using a Three-Sphere Model", *Proceedings of the Annual International Conference of the IEEE Engineering in Medicine and Biology Society,* 12(4): 1494–1495 (1990); Ferree and Tucker, "Development of High Resolution EEG Devices", *International Journal of Bioelectromagnetism,* 1(1) (1999); and Ferree, Ericksen and Tucker, "Regional Head Tissue Conductivity Estimation for Improved EEG Analysis", *Submitted to IEEE Transactions on Biomedical Engineering* (1999). Use of methods according to the present invention permit use of the same apparatus for measuring an individual's electrical activity as for characterizing the conductivity of the individual's body tissue. In research as well as clinical settings, this reduces time and cost.

An important application of methods according to the present invention is in electrical impedance plethysmography ("EIP"). In EIP, impedance characterizations made over time are used to localize changes in the body tissue. For example, when applied to the brain EIP may be used to show the location of a stroke, because internal bleeding changes the impedance at the locations of the bleeding. However, localizations of electrical sources may also be employed to characterize the effects of stroke. Moreover, it is good medical practice to corroborate diagnoses by the application of different types of testing. Accordingly, employing both impedance characterization methods and electrical source localization methods in the same apparatus according to the present invention, and also employing the methods at substantially the same time, i.e, contemporaneously with respect to the time frame during which significant changes occur in the body mass, provides for additional advantages in such applications.

The invention also provides for the advantage of adaptive refinement. Especially where impedance changes over time such that time for making measurements is a limited resource, it may be desirable to focus impedance characterization and source localization efforts on a particular sub-portion of the body volume. The aforedescribed methods provide for identifying a desired sub-portion quickly, by making relatively quick, gross conductivity and localization measurements. Thereafter, measurement resources can be applied more extensively to portions of the surface of the body corresponding particularly to the desired sub-portion, thereby neglecting other sub-portions that are not of particular interest. This refining process can be carried out in any number of iterative steps.

It is to be recognized that, while a particular method for localizing electrical activity in the body has been shown and described as preferred, other configurations could be utilized, in addition to configurations already mentioned, without departing from the principles of the invention.

The terms and expressions which have been employed in the foregoing specification are used therein as terms of description and not of limitation, and there is no intention of the use of such terms and expressions of excluding equivalents of the features shown and described or portions thereof, it being recognized that the scope of the invention is defined and limited only by the claims which follow.

We claim:

1. A method for localizing a source of electrical activity within a mass of body tissue, comprising:

applying a predetermined electrical stimulus to a portion of the surface of the body tissue at a first location;

measuring an actual complementary response to said electrical stimulus at the surface of the body tissue at a second location spaced from said first location;

removing said predetermined electrical stimulus from said first location; and measuring an actual complementary response to the source of electrical activity at the surface of the body tissue at substantially said second location.

2. The method of claim 1, further comprising estimating the conductivity of the mass of body tissue as a function of position therein by assuming a conductivity, calculating a complementary response to said electrical stimulus at said second location, comparing the calculated complementary response with the actual complementary response to said electrical stimulus to determine an error, and adjusting the assumed conductivity until the error is reduced to a predetermined acceptable amount.

3. The method of claim 1, further comprising estimating the strength and location of the source as a function of position in the mass of body tissue, calculating a complementary response to the source at said second location, comparing the calculated complementary response to the source with the actual complementary response to the source to determine an error, and adjusting the strength and location of the source until the error is reduced to a predetermined acceptable amount.

4. The method of claim 1, wherein said steps of measuring an actual complementary response to said electrical stimulus and measuring an actual complementary response to the source of electrical activity are performed at substantially the same time.

5. The method of claim 1, wherein said steps of applying said predetermined electrical stimulus at said first location, measuring said actual complementary response to said electrical stimulus at said second location, and measuring said actual complementary response to the source of electrical activity at substantially said second location are performed first to refine the location of the source to a sub-portion of the body, the method further comprising applying another predetermined electrical stimulus to a portion of the surface of the body tissue at a third location corresponding particularly to said sub-portion, measuring another actual complementary response to said other electrical stimulus at the surface of the body tissue at a fourth location also corresponding particularly to said sub-portion and spaced from said third location, removing said other predetermined electrical stimulus from said third location, and measuring another actual complementary response to the source of electrical activity at the surface of the body tissue at substantially said fourth location.

6. The method of claim 1, further comprising providing a carrier including two electrical devices, wherein a first of the electrical devices is adapted to carry out said step of applying said electrical stimulus and a second of the electrical devices is adapted to carry out both said steps of measuring said actual complementary response to said electrical stimulus and measuring said actual complementary response to the source of electrical activity.

7. The method of claim 6, wherein said carrier includes at least two additional electrical devices, wherein two of said at least two additional electrical devices and said first electrical device are arranged as vertices of a substantially equilateral triangle.

8. The method of claim 6, wherein said carrier includes at least two additional electrical devices, wherein two of said at least two additional electrical devices and said second electrical device are arranged as vertices of a substantially equilateral triangle.

* * * * *